United States Patent
Hamlin et al.

(10) Patent No.: US 9,827,207 B2
(45) Date of Patent: *Nov. 28, 2017

(54) PROPYNYLAMINOINDAN TRANSDERMAL COMPOSITIONS

(71) Applicant: Teikoku Pharma USA, Inc., San Jose, CA (US)

(72) Inventors: Richard D. Hamlin, Newark, CA (US); Amit Jain, Milpitas, CA (US); Jianye Wen, Palo Alto, CA (US)

(73) Assignee: Teikoku Pharma USA, Inc., San Jose, CA (US)

(*) Notice: Subject to any disclaimer, the term of this patent is extended or adjusted under 35 U.S.C. 154(b) by 25 days.

This patent is subject to a terminal disclaimer.

(21) Appl. No.: 14/933,598

(22) Filed: Nov. 5, 2015

(65) Prior Publication Data

US 2016/0051489 A1 Feb. 25, 2016

Related U.S. Application Data

(63) Continuation of application No. 14/064,006, filed on Oct. 25, 2013, now Pat. No. 9,205,061.

(60) Provisional application No. 61/722,044, filed on Nov. 2, 2012.

(51) Int. Cl.
*A61K 31/135* (2006.01)
*A61K 47/32* (2006.01)
*A61K 9/70* (2006.01)

(52) U.S. Cl.
CPC .......... *A61K 9/7061* (2013.01); *A61K 9/7084* (2013.01); *A61K 31/135* (2013.01)

(58) Field of Classification Search
None
See application file for complete search history.

(56) References Cited

U.S. PATENT DOCUMENTS

| | | | |
|---|---|---|---|
| 4,452,808 A | 6/1984 | Gallagher |
| 4,588,740 A | 5/1986 | Gallagher |
| 4,738,848 A | 4/1988 | Yoshida et al. |
| 4,824,860 A | 4/1989 | Owen |
| 4,912,126 A | 3/1990 | Owen |
| 5,176,916 A | 1/1993 | Yamanaka et al. |
| 5,387,612 A | 2/1995 | Youdim et al. |
| 5,391,406 A | 2/1995 | Ramharack et al. |
| 5,422,123 A | 6/1995 | Conte et al. |
| 5,453,446 A | 9/1995 | Youdim et al. |
| 5,457,133 A | 10/1995 | Youdim et al. |
| 5,462,746 A | 10/1995 | Wolter et al. |
| 5,519,061 A | 5/1996 | Youdim et al. |
| 5,532,415 A | 7/1996 | Youdim et al. |
| 5,543,151 A | 8/1996 | Shirai et al. |
| 5,576,353 A | 11/1996 | Youdim et al. |
| 5,599,991 A | 2/1997 | Youdim et al. |
| 5,650,165 A | 7/1997 | Akemi et al. |
| 5,668,181 A | 9/1997 | Youdim et al. |
| 5,683,710 A | 11/1997 | Akemi et al. |
| 5,744,500 A | 4/1998 | Youdim et al. |
| 5,786,390 A | 7/1998 | Youdim et al. |
| 5,807,570 A | 9/1998 | Chen et al. |
| 5,830,497 A | 11/1998 | Yamanaka et al. |
| 5,891,923 A | 4/1999 | Youdim et al. |
| 6,126,968 A | 10/2000 | Peskin et al. |
| 6,132,761 A | 10/2000 | Muraoka et al. |
| 6,146,656 A | 11/2000 | Hori et al. |
| 6,198,017 B1 | 3/2001 | Basedow et al. |
| 6,218,421 B1 | 4/2001 | King |
| 6,231,885 B1 | 5/2001 | Carrara |
| 6,262,330 B1 | 7/2001 | Fujisawa et al. |
| 6,300,365 B1 | 10/2001 | Holman |
| 6,316,504 B1 | 11/2001 | Youdim et al. |
| 6,528,685 B2 | 3/2003 | Cohen et al. |
| 6,562,363 B1 | 5/2003 | Mantelle et al. |
| 6,630,514 B2 | 10/2003 | Youdim et al. |
| 6,638,528 B1 | 10/2003 | Kanios |
| 6,689,379 B1 | 2/2004 | Bracht |
| 6,809,120 B1 | 10/2004 | Warrington et al. |
| 6,929,801 B2 | 8/2005 | Klose et al. |
| 6,936,661 B2 | 8/2005 | Koch et al. |
| 6,956,060 B2 | 10/2005 | Youdim et al. |
| 6,972,376 B2 | 12/2005 | Hughey et al. |
| 7,056,528 B1 | 6/2006 | Bracht |

(Continued)

FOREIGN PATENT DOCUMENTS

| CN | 101001616 A | 7/2007 |
|---|---|---|
| CN | 101032474 A | 9/2007 |

(Continued)

OTHER PUBLICATIONS

Schurad et al., Evaluation of the transdermal permeation behavior of Proterguride from drug in adhesive matrix patches through hairless mouse skin, Drug Dev Ind Pharm (2005), 31(6):505-13.

Furuishi et al, "Formulation and in Vitro Evaluation of Pentazocine Transdermal Delivery System", Biol. Pharm. Bull., 2008, 31(7):1439-1443.

Am et al., Contrasting neuroprotective and neurotoxic actions of respective metabolites of anti-Parkinson drugs rasagiline and selegiline, Neurosci Lett. Jan. 30, 2004;355(3):169-72.

(Continued)

*Primary Examiner* — Abigail Vanhorn

(74) *Attorney, Agent, or Firm* — Khin K. Chin; Bret E. Field; Bozicevic, Field & Francis LLP

(57) ABSTRACT

Propynylaminoindan (e.g., Rasagiline) transdermal compositions are provided. Aspects of the transdermal compositions include a matrix which includes the propynylaminoindan, a pressure sensitive adhesive that includes an acrylate copolymer and a cationic acrylic copolymer. Also provided are methods of using the transdermal compositions and kits containing the transdermal compositions.

18 Claims, 3 Drawing Sheets

(56) References Cited

U.S. PATENT DOCUMENTS

| | | |
|---|---|---|
| 7,070,808 B2 | 7/2006 | Govil et al. |
| 7,150,881 B2 | 12/2006 | Govil et al. |
| 7,175,853 B1 | 2/2007 | Bracht |
| 7,220,473 B2 | 5/2007 | Beier et al. |
| 7,335,379 B2 | 2/2008 | Carrara et al. |
| 7,375,249 B2 | 5/2008 | Boulton et al. |
| 7,378,439 B2 | 5/2008 | Tarur et al. |
| 7,396,860 B2 | 7/2008 | Blaugrund et al. |
| 7,491,847 B2 | 2/2009 | Frenkel et al. |
| 7,572,834 B1 | 8/2009 | Sterling et al. |
| 7,598,420 B1 | 10/2009 | Sterling et al. |
| 7,638,140 B2 | 12/2009 | Govil et al. |
| 7,989,496 B2 | 8/2011 | Hartwig et al. |
| 9,017,723 B2 * | 4/2015 | Wen .............. A61K 9/7061 424/487 |
| 9,205,061 B2 * | 12/2015 | Hamlin ............ A61K 9/7084 |
| 2003/0212085 A1 | 11/2003 | McCall et al. |
| 2004/0013620 A1 | 1/2004 | Klose et al. |
| 2004/0253299 A1 | 12/2004 | Beier et al. |
| 2005/0142175 A1 | 6/2005 | Langguth et al. |
| 2005/0175680 A1 | 8/2005 | Morgan et al. |
| 2005/0186141 A1 | 8/2005 | Gonda et al. |
| 2005/0187283 A1 | 8/2005 | Drago |
| 2005/0191348 A1 | 9/2005 | Youdim et al. |
| 2005/0245617 A1 | 11/2005 | Meyerson et al. |
| 2005/0267176 A1 | 12/2005 | Barberich |
| 2006/0078604 A1 | 4/2006 | Kanios et al. |
| 2006/0188581 A1 | 8/2006 | Peskin |
| 2007/0026054 A1 | 2/2007 | Theobald et al. |
| 2007/0078172 A1 | 4/2007 | McElroy et al. |
| 2007/0093495 A1 | 4/2007 | Ruggero et al. |
| 2007/0134310 A1 | 6/2007 | Nedberge et al. |
| 2007/0225379 A1 | 9/2007 | Carrara et al. |
| 2007/0254941 A1 | 11/2007 | Kumar et al. |
| 2007/0264319 A1 | 11/2007 | Lebo et al. |
| 2008/0004329 A1 | 1/2008 | Jamieson et al. |
| 2008/0089859 A1 | 4/2008 | Holman |
| 2008/0161408 A1 | 7/2008 | Frenkel et al. |
| 2008/0220092 A1 | 9/2008 | DiPierro et al. |
| 2008/0292708 A1 | 11/2008 | Stefanelli et al. |
| 2009/0035377 A1 | 2/2009 | Houze |
| 2009/0043111 A1 | 2/2009 | Liu |
| 2009/0062400 A1 | 3/2009 | Oron et al. |
| 2009/0076160 A1 | 3/2009 | Lendvai et al. |
| 2009/0136549 A1 | 5/2009 | Lin et al. |
| 2009/0136555 A1 | 5/2009 | Crowley et al. |
| 2009/0155343 A1 | 6/2009 | Kawahara et al. |
| 2009/0291127 A1 | 11/2009 | Wen et al. |
| 2009/0318564 A1 | 12/2009 | Frenkel et al. |
| 2010/0010095 A1 | 1/2010 | Frenkel |
| 2010/0016442 A1 | 1/2010 | Cohen et al. |
| 2010/0029987 A1 | 2/2010 | Allegrini et al. |
| 2010/0040690 A1 | 2/2010 | Govil et al. |
| 2010/0087768 A1 | 4/2010 | Forlano et al. |
| 2010/0285133 A1 | 11/2010 | Choi |
| 2011/0002976 A1 | 1/2011 | Yamamoto et al. |
| 2011/0268785 A1 | 11/2011 | Wen et al. |
| 2012/0265158 A1 | 10/2012 | Braun et al. |
| 2013/0072884 A1 | 3/2013 | Hamlin et al. |
| 2014/0170208 A1 | 6/2014 | Braun et al. |
| 2014/0186422 A1 * | 7/2014 | Hamlin .............. A61K 9/7084 424/443 |
| 2015/0182476 A1 * | 7/2015 | Wen .............. A61K 9/7061 424/443 |

FOREIGN PATENT DOCUMENTS

| | | |
|---|---|---|
| CN | 102475692 A | 5/2012 |
| EP | 593807 A1 | 4/1994 |
| EP | 887075 A2 | 12/1998 |
| EP | 2011488 A1 | 1/2009 |
| EP | 2172194 A1 | 4/2010 |
| EP | 2298277 A1 | 3/2011 |
| JP | H11-60475 A | 3/1999 |
| JP | 2005023088 A | 1/2005 |
| JP | 3731016 B2 | 1/2006 |
| JP | 2009529011 A | 8/2009 |
| JP | 2011051986 A1 | 3/2011 |
| WO | WO2000033812 A2 | 6/2000 |
| WO | WO2004012730 A1 | 2/2004 |
| WO | WO2005102393 A1 | 11/2005 |
| WO | WO2006012966 A1 | 2/2006 |
| WO | WO2008076348 A1 | 6/2008 |
| WO | WO2009030351 A2 | 3/2009 |
| WO | WO2009139411 A1 | 11/2009 |
| WO | WO2009152777 A1 | 12/2009 |
| WO | WO2011029598 A1 | 3/2011 |
| WO | WO2011139420 A2 | 11/2011 |
| WO | WO2012129429 | 9/2012 |

OTHER PUBLICATIONS

Duro-Tak and Gelva Transdermal Pressure Sensitive Adhesives, Product Selection Guide, Henkel, obtained online at: http://www.henkelna.com/us/content_data/330922_11061_LT5343_Product_selector2_Web863600.pdf, downloaded on Dec. 27, 2014.

* cited by examiner

PROPYNYLAMINOINDAN TRANSDERMAL COMPOSITIONS

CROSS-REFERENCE TO RELATED APPLICATIONS

This application is a continuation of U.S. application Ser. No. 14/064,006 filed on Oct. 25, 2013, which application, pursuant to 35 U.S.C. §119(e), claims priority to the filing date of U.S. Provisional Application Ser. No. 61/722,044 filed Nov. 2, 2012, the disclosures of which are herein incorporated by reference.

INTRODUCTION

Monoamine oxidases (MAOs) are enzymes that catalyze the oxidation of monoamines, such as monoaminergic neurotransmitters, including dopamine. Because of the role that MAOs play in the inactivation of neurotransmitters, MAO dysfunction (e.g., too much or too little MAO activity) is thought to be responsible for a number of neurological disorders. For example, unusually high or low levels of MAOs in the body have been associated with depression, schizophrenia, substance abuse, attention deficit disorder, migraines, and irregular sexual maturation.

MAOs are found in two main types, MAO type A (MAO-A) and MAO type B (MAO-B). MAO-B is more prevalent in the brain, where it is responsible for the breakdown of dopamine after its release into the synapse. Parkinson's disease is characterized by the death of cells that use dopamine to transmit their signals, which results in a decrease in overall synaptic signal strength and an increase in the symptoms associated with Parkinson's disease.

Rasagiline (i.e., (R)—N-(prop-2-ynyl)-2,3-dihydro-1H-inden-1-amine or R(+)—N-propargyl-1-aminoindan (trade name Azilect®)) is an irreversible inhibitor of monoamine oxidase (MAO) and is selective for MAO type B over MAO type A. By inhibiting the breakdown of dopamine in the synapse, rasagiline permits the signaling neurons to reabsorb more of the released dopamine for reuse later, which may compensate for the diminished quantities of dopamine being produced.

SUMMARY

Propynylaminoindan (e.g., Rasagiline) transdermal compositions are provided. Aspects of the transdermal compositions include a matrix which includes the propynylaminoindan, a pressure sensitive adhesive that includes an acrylate copolymer and a cationic acrylic copolymer. Also provided are methods of using the transdermal compositions and kits containing the transdermal compositions.

DETAILED DESCRIPTION

Figure 1:
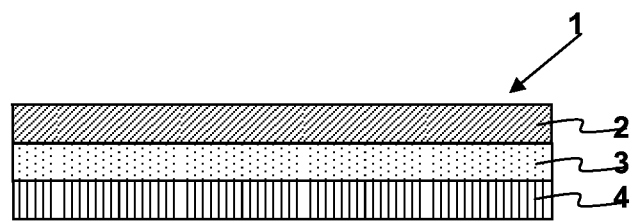
FIG. 1 shows a cross sectional view of an embodiment of the transdermal active agent formulation described herein.

Propynylaminoindan (e.g., Rasagiline) transdermal compositions are provided. Aspects of the transdermal compositions include a matrix which includes the propynylaminoindan, a pressure sensitive adhesive that includes an acrylate copolymer and a cationic acrylic copolymer. Also provided are methods of using the transdermal compositions and kits containing the transdermal compositions.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing various embodiments of the invention, aspects of the transdermal compositions are reviewed first in greater detail, followed by a detailed description of embodiments of using the transdermal delivery systems and a review of kits that include the transdermal delivery systems.

Propynylaminoindan Transdermal Compositions

As summarized above, propynylaminoindan transdermal compositions are provided. Transdermal compositions of the invention are formulations that are configured to transdermally deliver an active agent, specifically a propynylaminoindan, to a subject when topically applied to a skin surface of a subject. The compositions of the invention include a propynylaminoindan active agent layer, wherein the propynylaminoindan active agent layer is formulated to provide for multi-day delivery of a therapeutically effective amount of a propynylaminoindan active agent to a subject when the composition is topically applied to said subject. By multi-day delivery is meant that the layer is formulated to provide a therapeutically effective amount to a subject when the composition is applied to a skin site of a subject for a period of time that is 1 day or longer, such as 2 days or longer, e.g., 3 days or longer, such as 5 days or longer, including 7 days or longer, such as 10 days or longer. By therapeutically effective amount is meant that the compositions, when applied to a skin site of a subject during its intended time of application, e.g., within 7 days of application, provides for a systemic amount of propynylaminoindan that provides a desired therapeutic activity. In some embodiments, the compositions provide delivery of a target dosage of active agent that is 0.5 mg/day or greater over a one week period (i.e., 7 days or 168 hours), including 1.0 mg/day or greater over a one week period, such as 10 mg/day or greater over one week.

Transdermal compositions according to certain embodiments of the invention exhibit a therapeutically sufficient flux of the propynylaminoindan active agent over an extended period of time. The extended period of time over which substantially the flux is observed may vary, and in some instances is 24 hours or longer, such as 48 hours or longer, including 72 hours or longer, e.g., 96 hours or longer, including 120 hours or longer, such as 144 hours or longer, e.g., 168 hours or longer. While the actual flux may vary, in some instances (e.g., as determined using the skin permeation assay reported in the Experimental Section, below) skin permeation rates of 0.5 µg/cm$^2$/hr or greater, such as 1 µg/cm$^2$/hr or greater, including 2 µg/cm$^2$/hr or greater are provided by the compositions.

The size (i.e., area) of the transdermal compositions may vary. In certain embodiments, the size of the composition is chosen in view of the desired transdermal flux rate of the active agent and the target dosage. For example, if the transdermal flux is 3.4 µg/cm$^2$/hr and the target dosage is 5 mg/day, then the transdermal composition is chosen to have an area of about 43 cm$^2$. Or for example, if the transdermal flux is 3.4 µg/cm$^2$/hr and the target dosage is 10 mg/day, then the transdermal patch is chosen have an area of about 87 cm$^2$. In certain embodiments, the compositions have dimensions chosen to cover an area of skin when applied to a skin site that ranges from 10 to 200, such as 20 to 150, including 40 to 140 cm$^2$.

The propynylaminoindan active agent layer of the compositions may vary in thickness. In some instances, the thickness of the active agent layer (i.e., matrix) ranges from 25 to 250, such as 50 to 200, including 100 to 150 micrometers in thickness.

An aspect of the transdermal compositions according to certain embodiments of the invention is that they are storage stable. By storage-stable is meant that the compositions may be stored for extended periods of time without significant degradation and/or significant reduction in activity of the active agent. In certain embodiments, the subject compositions are stable for 6 months or longer, such as 1 year or longer, including 2 years or longer, e.g., 3 years or longer, etc., when maintained at 25° C. under sterile conditions. In some cases, the ratio of the amount of active in the composition to the initial amount of active agent in the composition after storage at about 60° C. for at least one month is 92% or more, 93% or more, such as 94% or more, including 95% or more, or greater, including 96% or greater, 97% or greater, 98% or greater, including 99% or greater.

In some embodiments, the compositions of the invention include a propynylaminoindan active agent layer, a backing layer and release liner. For example, FIG. 1 illustrates a composition 1 according to an embodiment of the invention, where the composition 1 includes a backing layer 2, a propynylaminoindan active agent layer 3 (i.e., matrix), and a release liner 4. While the matrix may in some instances be made up of two or more distinguishable layers, in some instances the matrix is a single uniform layer having a uniform composition throughout. Each of these layers is now described in greater detail.

Matrix

As reviewed above, transdermal compositions of invention include an active agent containing matrix present on a surface of a backing. Matrix layers of interest include an amount of propynylaminoindan active agent present in a pressure sensitive adhesive. Propynylaminoindans of interest include compounds that are described above the formula:

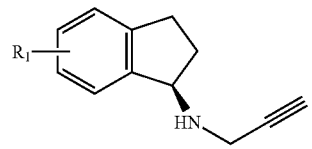

wherein $R_1$ is H, —$OR_2$, or

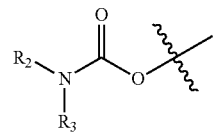

wherein $R_2$ is $C_1$-$C_4$ alkyl, and $R_3$ is H or $C_1$-$C_4$ alkyl. In some instances, the propynylaminoindan is N-propargyl-1-aminoindan (i.e., Rasagiline).

The propynylaminoindan active agent may be present in the matrix as a free base or salt. Pharmaceutically acceptable salts include, but are not limited to, the mesylate, maleate, fumarate, tartrate, hydrochloride, hydrobromide, esylate, p-toluenesulfonate, benzoate, acetate, phosphate and sulfate salts. In addition, the propynylaminoindan may be present as a racemic mixture or as a pure enantiomer, such as the R or L enantiomer of the active agent.

In some instances, the propynylaminoindan in the matrix is solely R(+)—N-propargyl-1-aminoindan free base. In some instances, the propylnylaminoindan is solely R(+)—N-propargyl-1-aminoindan mesylate.

The amount of the propynylaminoindan present in the matrix may vary. In certain embodiments, the amount may be 5% or more by weight, such as 10% or more by weight, e.g., 14% or more by weight. In some instances, the amount of propynylaminoindan in a given transdermal formulation may range from 5 mg to 50 mg, such as 10 mg to 40 mg and including 15 mg to 30 mg.

As reviewed above, the matrix includes a pressure sensitive adhesive. The terms "pressure sensitive adhesive", "self adhesive", and "self stick adhesive" mean an adhesive that forms a bond when pressure is applied to adhere the adhesive with a surface. In some instances, the adhesive is one in which no solvent, water, or heat is needed to activate the adhesive. For pressure sensitive adhesives, the degree of bond strength is proportional to the amount of pressure that is used to apply the adhesive to the surface.

Pressure sensitive adhesives of interest include acrylate copolymers present in an organic solvent. Acrylate copolymers of interest include copolymers of various monomers which may be "soft" monomers, "hard" monomers, and optionally "functional" monomers. Also of interest are blends including such copolymers. The acrylate copolymers can be composed of a copolymer including bipolymer (i.e., made with two monomers), a terpolymer (i.e., made with three monomers), or a tetrapolymer (i.e., made with four monomers), or copolymers made from even greater numbers of monomers. The acrylate copolymers can include cross-linked and non-cross-linked polymers. The polymers can be cross-linked by known methods to provide the desired polymers.

Monomers from which the acrylate copolymers are produced include at least two or more exemplary components selected from the group including acrylic acids, alkyl acrylates, methacrylates, copolymerizable secondary monomers. Monomers ("soft" and "hard" monomers) of interest include, but are not limited to, methoxyethyl acrylate, ethyl acrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, acrylonitrile, methoxyethyl acrylate, methoxyethyl methacrylate, and the like. Additional examples of acrylic adhesive monomers are described in Satas, "Acrylic Adhesives," Handbook of Pressure-Sensitive Adhesive Technology, 2nd ed., pp. 396-456 (D. Satas, ed.), Van Nostrand Reinhold, N.Y. (1989). Acrylic adhesives, available from several commercial sources, are sold under the trade names AROSET, DUROTAK, EUDRAGIT, GELVA, and NEOCRYL.

Organic solvents of interest that may be present in the pressure sensitive adhesive component of the matrix (at least during preparation and before any drying during manufacture, e.g., as described below in the experimental section) may vary. Organic solvents of interest include, but are not limited to: ethyl acetate, heptane, hexane, cyclohexane, methyl alcohol, ethyl alcohol, isopopropyl alcohol, acetyl acetone, toluene and xylene. The percent solids in the pressure sensitive adhesive may vary, ranging in some instances from 35 to 65%, such as 35 to 50%.

Of interest in some instances are pressure sensitive adhesives in which the acrylate polymers of the adhesive lack pendant functional groups, such as —OH, —COOH, etc. In some embodiments, the adhesive may have a composition that is, or is substantially the same as, the composition of DuroTak® 87-9301 (Henkel, Bridgewater, N.J.). The term "substantially the same" as used herein refers to a composition that is an acrylate copolymer lacking —COOH functional groups in an organic solvent solution and provides for the functionality as described herein. Specifically, of interest is a pressure sensitive adhesive composition which includes an acrylate copolymer that lacks functional groups and is present in a solvent system that includes both ethyl acetate and cyclohexane, where the percent solids in the composition ranges from 30 to 40%, such as 33 to 37%, e.g., 36%. In some embodiments, the acrylic pressure-sensitive adhesive is DuroTak® 87-9301. In some embodiments, the adhesive may have a composition that is, or is substantially the same as, the composition of Gelva 7883, a pressure sensitive adhesive which includes an acrylate vinyl acetate that lacks COOH groups.

In some instances, the pressure sensitive adhesive comprising a polymer that lacks functional groups may make up from 50 to 95, such as 60 to 90 and including 75 to 90% by weight of the matrix.

When the propynylaminoindan is present as a free base, the matrix may consist of the active agent and pressure sensitive adhesive, such as DuroTak® 87-9301 or Gelva 7883 pressure sensitive adhesives.

In some instances, e.g., where the propynylaminoindan is present as a salt, the matrix may further include a weak base, such as a cationic acrylic copolymer. Cationic acrylic copolymers of interest are polymers of two or more different monomeric residues, where at least one of the residues is an acrylic residue, e.g., an acrylate or a methacrylate, and at least one of the residues includes a cationic pendant group, e.g., an amino pendant group, where these features may be includes in the same or different monomeric residues making up the copolymer. Where desired, the cationic acrylic copolymer may be aminated methacrylate copolymer. The aminated methacrylate copolymer may be a copolymer of diethylaminoethyl methacrylate, butyl methacrylate and methyl methacrylate, e.g., present in a 2:1:1 ratio. In some instances, the aminated methacrylate copolymer may be described by the formula:

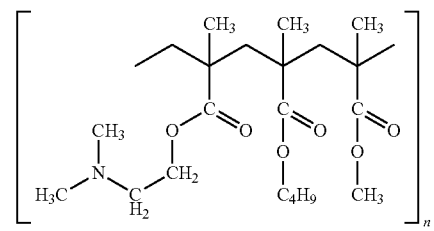

In some instances, the average molecular weight of the aminated methacrylate copolymer ranges from 25,000 to 75,000 daltons, such as 30,000 to 60,000 daltons, including 45,000 to 55,000 daltons Of interest are aminated methacrylate copolymers that are substantially the same as Eudragit® E100, Eudragit® E PO and/or Eudragit® E 12.5 aminated methacrylate copolymers. As used herein, the term substantially the same is meant that the aminated methacrylate copolymer has the same functional impact on the composition as Eudragit® E100, Eudragit® E PO and/or Eudragit® E 12.5 aminated methacrylate copolymers. In some instances, the aminated methacrylate copolymer is Eudragit® E100, Eudragit® E PO and/or Eudragit® E 12.5 aminated methacrylate copolymers. If present, the amount of cationic acrylic copolymer may be present in an amount ranging from 1 to 15, such as 2 to 10 and including 4 to 8% by weight of the matrix. Also of interest as weak bases are agents such as triethanolamine. If present, the amount of triethanolamine may be present in an amount ranging from 1 to 15, such as 2 to 10 and including 2 to 8% by weight of the matrix, such as 2 to 4% by weight of the matrix.

In some instances, the matrix may further include one or more additional pressure sensitive adhesives which exhibit functionality, e.g., by including acrylate copolymers having polar functional monomeric residues. Of interest are pressure sensitive adhesive that have polymers with monomeric residues that provide for —COOH functional groups, i.e., residues that have pendant —COOH groups. In other words, the polymer includes residues having attached —COOH groups. Useful carboxylic acid monomers to provide the —COOH functional group and from which the polymers of such adhesives may be prepared may contain from about 3 to about 6 carbon atoms and include, among others, acrylic acid, methacrylic acid, itaconic acid, and the like. Acrylic acid, methacrylic acid and mixtures thereof are employed in certain embodiments. In some embodiments, the adhesive may include an —COOH functional group containing acylate copolymer that is the same as, or substantially the same as, DuroTak® 87-2353; DuroTak® 87-2052; DuroTak® 87-2979; DuroTak® 87-2074; DuroTak® 87-235A; DuroTak® 87-2852; DuroTak® 87-2051; DuroTak® 87-2054; DuroTak® 87-2677; DuroTak® 87-2194; DuroTak® 87-2196; and DuroTak® 87-2825 (Henkel, Bridgewater, N.J.). In some embodiments, this additional pressure sensitive adhesive may be the same as or substantially the same as DuroTak® 87-2353; DuroTak® 87-2052; DuroTak® 87-2979; DuroTak® 87-2074; DuroTak® 87-235A; DuroTak® 87-2852; DuroTak® 87-2051; DuroTak® 87-2054; DuroTak® 87-2677; DuroTak® 87-2194; DuroTak® 87-2196; or DuroTak® 87-2825 (Henkel, Bridgewater, N.J.). The term "substantially the same" as used herein refers to a composition that is an acrylate-vinyl acetate copolymer in an organic solvent solution and provides for the functionality as described herein. If present, the amount of such additional pressure sensitive adhesives having polymers with carboxyl functional groups will, in some instances, be present in an amount that is 35% or less, such as 30% or less, including 25% or less, e.g., 20% or less by weight of the matrix, and may be present in an amount ranging from 1 to 15, such as 2 to 10% by weight of the matrix.

The matrix as described herein may contain a percutaneous absorption enhancer. The percutaneous absorption enhancer may facilitate the absorption of the active agent by the skin of the subject. The percutaneous absorption enhancer may also be referred to as a percutaneous permeation enhancer because it may facilitate not only the percutaneous absorption of the active agent, but also the percutaneous permeation of the active agent through the skin of the subject.

The percutaneous absorption enhancer may include, but is not limited to the following: aliphatic alcohols, such as but not limited to saturated or unsaturated higher alcohols having 12 to 22 carbon atoms, such as oleyl alcohol and lauryl alcohol; fatty acids, such as but not limited to linolic acid, oleic acid, linolenic acid, stearic acid, isostearic acid and palmitic acid; fatty acid esters, such as but not limited to isopropyl myristate, diisopropyl adipate, and isopropyl palmitate; alcohol amines, such as but not limited to triethanolamine, triethanolamine hydrochloride, and diisopropanolamine; polyhydric alcohol alkyl ethers, such as but not limited to alkyl ethers of polyhydric alcohols such as glycerol, ethylene glycol, propylene glycol, 1,3-butylene glycol, diglycerol, polyglycerol, diethylene glycol, polyethylene glycol, dipropylene glycol, polypropylene glycol, sorbitan, sorbitol, isosorbide, methyl glucoside, oligosaccharides, and reducing oligosaccharides, where the number of carbon atoms of the alkyl group moiety in the polyhydric alcohol alkyl ethers is preferably 6 to 20; polyoxyethylene alkyl ethers, such as but not limited to polyoxyethylene alkyl ethers in which the number of carbon atoms of the alkyl group moiety is 6 to 20, and the number of repeating units (e.g. —O—$CH_2CH_2$—) of the polyoxyethylene chain is 1 to 9, such as but not limited to polyoxyethylene lauryl ether, polyoxyethylene cetyl ether, polyoxyethylene stearyl ether, and polyoxyethylene oleyl ether; glycerides (i.e., fatty acid esters of glycerol), such as but not limited to glycerol esters of fatty acids having 6 to 18 carbon atoms, where the glycerides may be monoglycerides (i.e., a glycerol molecule covalently bonded to one fatty acid chain through an ester linkage), diglycerides (i.e., a glycerol molecule covalently bonded to two fatty acid chains through ester linkages), triglycerides (i.e., a glycerol molecule covalently bonded to three fatty acid chains through ester linkages), or combinations thereof, where the fatty acid components forming the glycerides include, but are not limited to octanoic acid, decanoic acid, dodecanoic acid, tetradecanoic acid, hexadecanoic acid, octadecanoic acid (i.e., stearic acid) and oleic acid; middle-chain fatty acid esters of polyhydric alcohols; lactic acid alkyl esters; dibasic acid alkyl esters; acylated amino acids; pyrrolidone; pyrrolidone derivatives; and combinations thereof.

Additional types of percutaneous absorption enhancers include, but are not limited to lactic acid, tartaric acid, 1,2,6-hexanetriol, benzyl alcohol, lanoline, potassium hydroxide (KOH), and tris(hydroxymethyl)aminomethane.

Specific examples of percutaneous absorption enhancers include, but are not limited to glycerol monooleate (GMO), sorbitan monolaurate (SML), sorbitan monooleate (SMO), laureth-4 (LTH), and combinations thereof.

In some cases, the matrix contains the percutaneous absorption enhancer in an amount ranging from 2% to 25% (w/w), such as from 5% to 20% (w/w), and including from 5% to 15% (w/w). In certain cases, the matrix contains the percutaneous absorption enhancer in an amount of about 5% (w/w), about 10% (w/w), about 15% (w/w), or about 20% (w/w).

In some embodiments, the matrix layer is insoluble in water. By insoluble in water is meant that that the matrix layer may be immersed in water for a period of 1 day or longer, such as 1 week or longer, including 1 month or longer, and exhibit little if any dissolution, e.g., no observable dissolution.

Backing

As summarized above, transdermal compositions of interest may include a backing (i.e., support layer). The backing may be flexible to an extent that it can be brought into close contact with a desired topical location of a subject. The backing may be fabricated from a material that it does not absorb the active agent, and does not allow the active agent to be released from the side of the support. The backing may include, but is not limited to, non-woven fabrics, woven fabrics, films (including sheets), porous bodies, foamed bodies, paper, composite materials obtained by laminating a film on a non-woven fabric or fabric, and combinations thereof.

Non-woven fabric may include, but is not limited to, the following: polyolefin resins such as polyethylene and polypropylene; polyester resins such as polyethylene terephthalate, polybutylene terephthalate and polyethylene naphthalate; rayon, polyamide, poly(ester ether), polyurethane, polyacrylic resins, polyvinyl alcohol, styrene-isoprene-styrene copolymers, and styrene-ethylene-propylene-styrene copolymers; and combinations thereof. Fabrics may include, but are not limited to: cotton, rayon, polyacrylic resins, polyester resins, polyvinyl alcohol, and combinations thereof. Films may include, but are not limited to the following: polyolefin resins such as polyethylene and polypropylene; polyacrylic resins such as polymethyl methacrylate and polyethyl methacrylate; polyester resins such as polyethylene terephthalate, polybutylene terephthalate and polyethylene naphthalate; and besides cellophane, polyvinyl alcohol, ethylene-vinyl alcohol copolymers, polyvinyl chloride, polystyrene, polyurethane, polyacrylonitrile, fluororesins, styrene-isoprene-styrene copolymers, styrene-butadiene rubber, polybutadiene, ethylene-vinyl acetate copolymers, polyamide, and polysulfone; and combinations thereof. Papers may include, but are not limited to, impregnated paper, coated paper, wood free paper, Kraft paper, Japanese paper, glassine paper, synthetic paper, and combinations thereof. Composite materials may include, but are not limited to, composite materials obtained by laminating the above-described film on the above-described non-woven fabric or fabric.

The size of the backing may vary, and in some instances the backing is sized to cover the desired topical target site. In some embodiments, the backing has a length ranging from 2 to 100 cm, such as 4 to 60 cm and a width ranging from 2 to 100 cm, such as 4 to 60 cm.

In some embodiments, the backing layer is insoluble in water. By insoluble in water is meant that that the backing layer may be immersed in water for a period of 1 day or longer, such as 1 week or longer, including 1 month or longer, and exhibit little if any dissolution, e.g., no observable dissolution.

Release Liner

In some embodiments, a release liner is provided on the active agent layer (i.e., matrix), and specifically on a surface of the active agent layer that is distal (i.e. opposite) from the backing layer, if present. The release liner facilitates the protection of the active agent layer. The release liner may be prepared by treating one side of polyethylene-coated wood free paper, polyolefin-coated glassine paper, a polyethylene terephthalate (polyester) film, a polypropylene film, or the like with a silicone treatment.

Adhesive Overlay

Optionally, one or more adhesive overlays can be used to increase the adhesion of the composition when applied to the skin. Adhesive overlays can include a layer of adhesive present on a backing material, such as a porous, non-porous, occlusive, or breathable backing material. The dimensions of the adhesive overlay are chosen to provide the desired functionality, where in some instances the dimensions are chose such that the adhesive overlay, when applied over the active agent formulation, extends some distance beyond one or more of the sides of the active agent formulation. In some instances, the area of the adhesive overlay exceeds the area of the active agent formulation by 5% or more, such as by 10% or more, including by 20% or more. During use, the adhesive overlay can be applied by the patients, by the care givers, or can be integrated in the kits.

Methods of Use

Methods of using the product transdermal compositions include administering an effective amount of the propynylaminoindan composition to a subject in order to treat the subject for a target condition of interest, e.g., as described in the Utility section below. By "treating" or "treatment" is meant at least a suppression or an amelioration of the symptoms associated with the condition afflicting the subject, where suppression and amelioration are used in a broad sense to refer to at least a reduction in the magnitude of a parameter, e.g., symptom, associated with the condition being treated. As such, treatment also includes situations where the condition is completely inhibited, e.g., prevented from happening, or stopped, e.g., terminated, such that the subject no longer experiences the condition. As such, treatment includes both preventing and managing a condition.

In practicing the methods, the transdermal compositions disclosed herein can be topically administered to a subject, i.e., the transdermal compositions may be administered to any convenient topical site (e.g., skin site). Topical sites of interest include both mucosal sites and keratinized skin sites, and therefore include, but are not limited to: mouth, nose, eyes, rectum, vagina, arms, leg, torso, head, etc. The surface area that is covered by the topical composition following application is sufficient to provide for the desired amount of agent administration, and in some embodiments ranges from 1 to 200 $cm^2$, such as from 10 to 180 $cm^2$, and including from 100 to 150 $cm^2$, e.g., 140 $cm^2$.

The transdermal composition may be maintained at the topical site to which it has been applied for a desired amount of time, e.g., to deliver a desired amount of active agent delivery. In some instances, the period of time that the composition is maintained at the site of application is 24 hours or longer, such as 48 hours or longer, e.g., 72 hours or longer, such as 96 hours or longer.

In practicing the subject methods, a given dosage of the transdermal composition may be applied a single time or a plurality of times over a given time period, e.g., the course of the disease condition being treated, where the dosing schedule when a plurality of compositions are administered over a given time period may be daily, weekly, biweekly, monthly, etc.

The area of skin covered by the topical composition when applied may vary. In some instances, the area of skin covered by the topical composition upon application ranges from 1 to 200 $cm^2$, such as 10 to 180 $cm^2$ and including 100 to 150 $cm^2$.

After the transdermal active agent composition has been applied to the skin site for the desired amount of time (i.e., an amount of time sufficient to deliver a target dose of the active agent to the subject over a period of time), the composition may be removed from the skin site. A new transdermal composition may be applied at the same or at a different skin site. The new transdermal composition may be applied to a different skin site to reduce the possible occurrence of skin irritation and/or skin sensitization at the prior site of application.

In certain embodiments, the subject methods include a diagnostic step. Individuals may be diagnosed as being in need of the subject methods using any convenient protocol. In addition, individuals may be known to be in need of the subject methods, e.g., they are suffering from Parkinson's disease. Diagnosis or assessment of target condition can be performed using any convenient diagnostic protocol.

Methods of the invention may further include assessing the efficacy of the treatment protocol that includes administration of the local anesthetic emulsion composition. Assessing the efficacy of treatment may be performed using any convenient protocol.

In some instances, transdermal compositions may be administered in conjunction with one or more additional therapies specific for the target condition of interest. As such, the transdermal compositions may be used alone to treat the target disorder, or alternatively, as in the case of Parkinson's disease, for example, they may be used as an adjunct to the conventional L-DOPA treatments.

Transdermal compositions of the invention may be administered to a variety of different types of subjects. Subjects of interest include, but are not limited to: mammals, both human and non-human, including the orders carnivore (e.g., dogs and cats), rodentia (e.g., mice, guinea pigs, and rats), lagomorpha (e.g. rabbits) and primates (e.g., humans, chimpanzees, and monkeys). In certain embodiments, the subjects, e.g., patients, are humans.

Utility

The transdermal compositions of the invention find use in any application where a subject would benefit from being transdermally administered a propynylaminoindan, such as rasagiline. Rasagiline and/or its salts find use in the treatment of a variety of different disease conditions, such as but not limited to: Parkinson's disease, Alzheimer's Disease, memory disorders, stroke and other disorders, e.g., as described in U.S. Pat. Nos. 5,387,612; 5,453,446; 5,457,133; 5,668,181; 5,576,353; 5,532,415; 5,599,991; 5,786,390; 5,519,061; 5,891,923; 5,744,500 and 6,316,504, the contents of which are hereby incorporated by reference. By treatment is meant that at least an amelioration of the symptoms associated with the condition afflicting the subject is achieved, where amelioration is used in a broad sense to refer to at least a reduction in the magnitude of a parameter, e.g., symptom, associated with the condition being treated. As such, treatment also includes situations where the pathological condition, or at least symptoms associated therewith, are completely inhibited, e.g., prevented from happening, or stopped, e.g., terminated, such that the subject no longer suffers from the condition, or at least the symptoms that characterize the condition.

Kits

Kits for use in practicing certain methods described herein are also provided. In certain embodiments, the kits include one or more transdermal compositions as described above. In certain embodiments, the kits include an adhesive overlay as described above. In some embodiments, the kits include multilayers such as a layer containing drug and a layer that may or may not contain any drug and other excipients. In a given kit that includes two or more compositions, the compositions may be individually packaged or present within a common container.

In certain embodiments, the kits will further include instructions for practicing the subject methods or means for obtaining the same (e.g., a website URL directing the user to a webpage which provides the instructions), where these instructions may be printed on a substrate, where substrate may be one or more of: a package insert, the packaging, reagent containers and the like. In the subject kits, the one or more components are present in the same or different containers, as may be convenient or desirable.

The following examples are offered by way of illustration and not by way of limitation. Specifically, the following examples are of specific embodiments for carrying out the present invention. The examples are for illustrative purposes only, and are not intended to limit the scope of the present invention in any way.

EXAMPLES

I. Materials and Methods

A. Preparation of Active Agent Reservoir Layer

Formulations were prepared by mixing stock solutions of each of the mixture components in organic solvents (typically 30-60 wt % solid content in ethyl acetate, methanol and/or ethanol), followed by a mixing process. Once a homogeneous mixture was formed, the solution was cast on a release liner (siliconized polyester sheet of 2-3 mils) and dried at 65°-80° C. for 10-90 minutes. The adhesive films were laminated to a PET backing.

B. Transdermal Flux Tests

Human cadaver skin was used and epidermal layers (stratum corneum and epidermis) were separated from the full-thickness skin as skin membrane. Samples were die-cut with an arch punch to a final diameter of about 2.0 cm$^2$. The release liner was removed and the system was placed on top of the epidermis/stratum corneum with the drug adhesive layer facing the stratum corneum. Gentle pressure was applied to effect good contact between the adhesive layer and stratum corneum. The donor and receptor sides of the Franz cell were clamped together and the receptor solution containing a phosphate buffer at pH 6.5 was added to the Franz cell. The cells were kept at 33° C. for the duration of the experiment. Samples of the receptor solution were taken at regular intervals and the active agent concentration was measured by HPLC. The removed receptor solution was replaced with fresh solution to maintain the sink conditions. The flux was calculated from the slope of cumulative amounts of the drug in the receiver compartment versus time plot.

C. Specific Examples

Figure 2A:
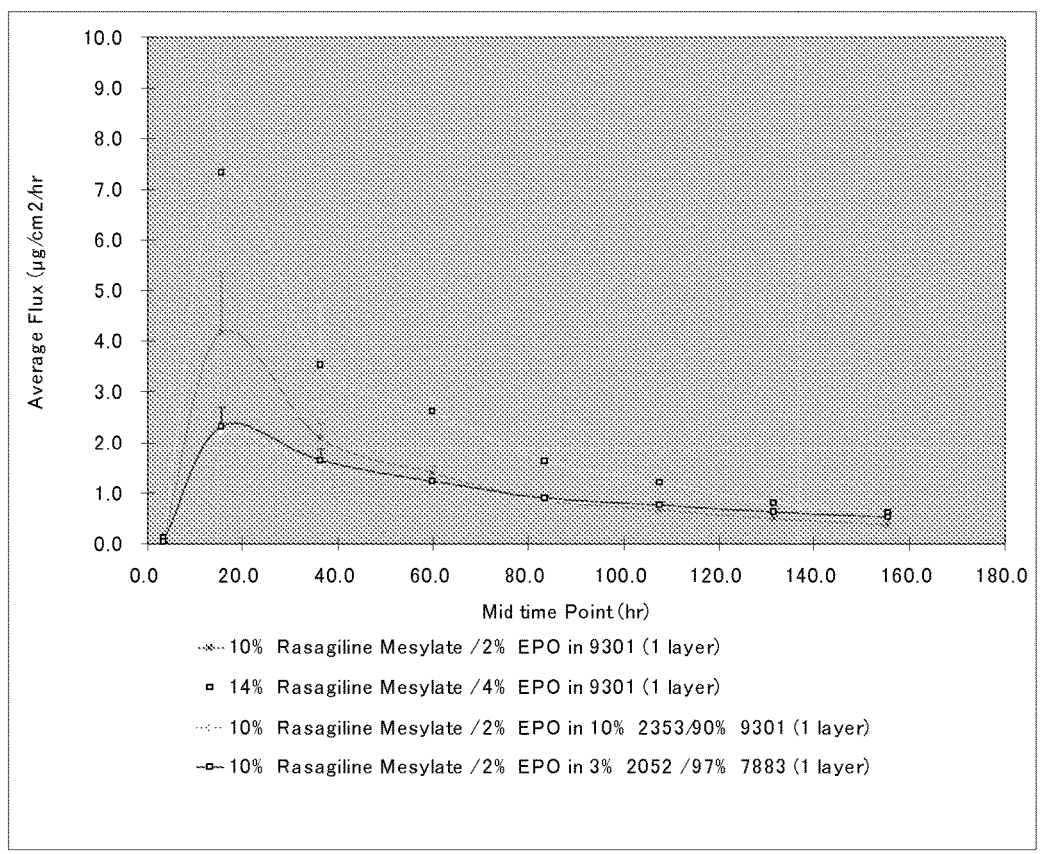
FIGS. 2A to 2B provide graphs of flux as a function of time (middle point between the two sampling time points) for various formulations.
Figure 2B:
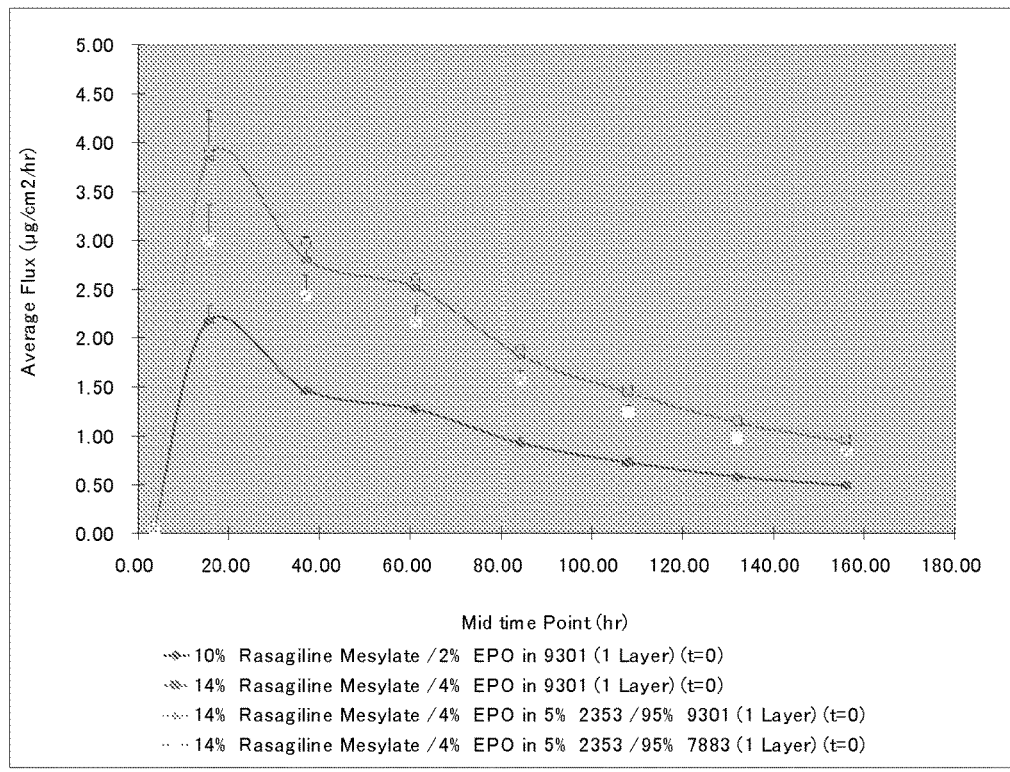

C.1 Flux of Various Transdermal Formulations that Include Rasagiline Mesylate in an Acrylate Adhesive Using the general method described above, a series of transdermal systems containing different amounts of one or more of: Rasagiline, Duro-tak® 87-2353, 87-2052 and/or 87-9301, and Eudragit E PO were prepared with details shown in the following table. In addition, one formulation was prepared in which Gelva 7883 (an acrylate vinyl acetate) was employed. The flux through human cadaver skin was measured and the results are graphically presented in FIGS. 2A and 2B.

TABLE 1

| | % by weight | | | | | |
|---|---|---|---|---|---|---|
| | Form. 1 | Form. 2 | Form. 3 | Form. 4 | Form. 5 | Form. 6 |
| Rasagiline Mesylate | 10 | 10 | 10 | 14 | 14 | 14 |
| EPO | 2 | 2 | 2 | 4 | 4 | 4 |
| 2353 (—COOH, no crosslinked) | | 8.8 | | | 4.1 | 4.1 |

TABLE 1-continued

|  | % by weight | | | | | |
| --- | --- | --- | --- | --- | --- | --- |
|  | Form. 1 | Form. 2 | Form. 3 | Form. 4 | Form. 5 | Form. 6 |
| 2052 (—COOH, crosslinked) |  |  | 2.64 |  |  |  |
| 9301 (No —COOH) | 88 | 79.2 |  | 82 | 77.9 |  |
| Gelva 7883 (acrylate vinyl acetate; No—COOH) |  |  | 85.36 |  |  | 77.9 |
| Total | 100 | 100 | 100 | 100 | 100 | 100 |

C.2 Stability

Stability was determined as follows. The Rasagiline Mesylate test patches were prepared at 4 cm² size and pouched in Polyacrylonitrile (PAN) material. The patches were stored at room temperature, 30° C. and 40° C. temperatures chambers (w/o humidity control). The pouch material used was purchased from Dia Nippon.

At selected time pointd, the patches were extracted to determine Rasagiline Mesylate and 1-Aminoindan (main degradent) concentration. The stability of the patches was determined by high performance liquid chromatography (HPLC). The results are provided in the tables below.

TABLE 2

| | | % Recovery (Relative to initial) | | | | |
| --- | --- | --- | --- | --- | --- | --- |
| Sample | Condition | T = 0 API | 1 month API | 2 month API | 3 month API | 6 month API |
| 10% Rasagiline Mesylate, 2% E PO in 9301 (Lot: 094-51-1) % Theoretical: 100.3 | RT | 100 | 99 | 98.4 | 97.4 | |
| | 40° C. | — | 101.8 | 97.9 | 96.7 | |
| 14% Rasagiline Mesylate, 4% E PO in 9301 (Lot: 094-51-2) % Theoretical: 99.5 | RT | 100 | 101.6 | 99.2 | 101.2 | |
| | 40° C. | — | 100.9 | 102.4 | 99.6 | |
| 10% Rasagiline Mesylate, 2% E PO in 10% 2353/ 90% 9301 (Lot: 094-51-3) % Theoretical: 99.2 | RT | 100 | 101.2 | 99.2 | 98.9 | |
| | 40° C. | — | 99.1 | 96.7 | 97.5 | |
| 10% Rasagiline Mesylate, 2% E PO in 3% 2052/ 97% 7883 (Lot: 094-51-4) % Theoretical: 96.4 | RT | 100 | 98.4 | 98.6 | 96.6 | |
| | 40° C. | — | 99.1 | 97 | 95.5 | |

TABLE 3

| | | % Recovery (Relative to initial) | | | | |
| --- | --- | --- | --- | --- | --- | --- |
| Sample | Condition | T = 0 API | 1 month API | 2 month API | 3 month API | 6 month API |
| 10% Rasagiline Mesylate, 2% E PO in 9301 (Lot: 094-69-1) % Theoretical: 99.1 | RT | 100 | 99.8 | | | |
| | 40° C. | — | 97.2 | | | |
| 14% Rasagiline Mesylate, 4% E PO in 9301 (Lot: 094-69-2) % Theoretical: 97.0 | RT | 100 | 97.2 | | | |
| | 40° C. | — | 100.3 | | | |
| 14% Rasagiline Mesylate, 4% E PO in 5% 2353/ 95% 9301 (Lot: 094-69-3) % Theoretical: 96.6 | RT | 100 | 99.6 | | | |
| | 40° C. | — | 98.8 | | | |
| 14% Rasagiline Mesylate, 4% E PO in 5% 2353/ 95% 7883 (Lot: 094-69-4) % Theoretical: 96.3 | RT | 100 | 98.8 | | | |
| | 40° C. | — | 97.2 | | | |

TABLE 4

| | | % Recovery (Relative to initial) | | | | |
|---|---|---|---|---|---|---|
| Sample | Condition | T = 0 API | 1 month API | 2 month API | 3 month API | 6 month API |
| 10% Rasagiline Mesylate, | RT | 100 | 100.8 | 99.5 | 100.5 | 100.1 |
| 2% E PO in 33% | 30° C. | — | 97.9 | 98.5 | 97.5 | 97.5 |
| 2100/67% 2999 | 40° C. | — | 97.3 | 94.8 | 94.5 | 95.5 |
| (Lot: 094-39-4) | | | | | | |
| 10% Rasagiline Mesylate, | RT | 100 | 98.5 | 97.2 | 98.4 | 97.7 |
| 2% E PO, 0.5% BHT in | 30° C. | — | 95.6 | 96.3 | 96.3 | 95.7 |
| 33% 2100/67% 2999 | 40° C. | — | 95.6 | 95.4 | 94.7 | 92.3 |
| (Lot: 094-39-5) | | | | | | |
| 10% Rasagiline Mesylate, | RT | 100 | 98.3 | 101.1 | 101.1 | 101.3 |
| 2% E PO in 9301 | 30° C. | — | 99.9 | 101.6 | 101.2 | 100.7 |
| (Lot: 094-39-8) | 40° C. | — | 100.8 | 99.8 | 101.2 | 100.8 |

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A transdermal composition, the composition comprising:
   (A) a matrix comprising:
   (i) a propynylaminoindan; and
   (ii) a pressure sensitive adhesive consisting of:
      ($a_1$) an acrylate copolymer that lacks pendant functional groups or
      ($a_2$) an acrylate copolymer component that consists of one or more acrylate copolymers that lacks pendant functional groups; and
   (b) a cationic acrylic copolymer component; and
   (B) a backing.

2. The transdermal composition according to claim 1, wherein the propynylaminoindan is rasagiline.

3. The transdermal composition according to claim 2, wherein rasagiline is present as a free base.

4. The transdermal composition according to claim 2, wherein the rasagiline is present as a salt.

5. The transdermal composition according to claim 4, wherein the salt is rasagiline mesylate.

6. The transdermal composition according to claim 5, wherein the acrylate copolymer component is an acrylate copolymer that lacks pendant functional groups in a solvent system comprising ethyl acetate and cyclohexane.

7. The transdermal composition according to claim 5, wherein the acrylate copolymer component is an acrylate vinyl acetate that lacks —COOH functional groups.

8. The transdermal composition according to claim 1, wherein the pressure sensitive adhesive is present in an amount ranging from 75 to 90% by weight of the matrix.

9. The transdermal composition according to claim 1, wherein the cationic acrylic copolymer is an aminated methacrylate copolymer.

10. The transdermal composition according to claim 9, wherein the aminated methacrylate copolymer is a copolymer of diethylaminoethyl methacrylate, butyl methacrylate and methyl methacrylate.

11. The transdermal composition according to claim 10, wherein the aminated methacrylate copolymer is described by the formula:

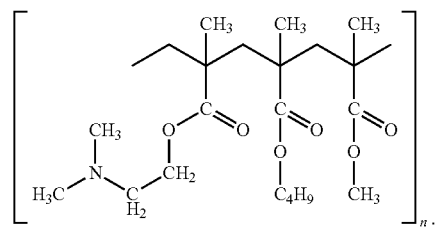

12. The transdermal composition according to claim 1, wherein the matrix comprises an enhancer.

13. The transdermal composition according to claim 1, wherein the transdermal composition exhibits a therapeutic flux of the propynylaminoindan over an extended period of time.

14. The transdermal composition according to claim 1, wherein the matrix has a single layer configuration.

15. The transdermal composition according to claim 1, wherein the composition further comprises a release liner.

16. The transdermal composition according to claim 1, wherein the composition is storage stable.

17. A method comprising:
   applying to a skin surface of a subject a transdermal composition according to claim 1 in a manner sufficient to achieve a therapeutic flux of the propynylaminoindan over an extended period of time.

18. A kit comprising two or more transdermal compositions according to claim 1.

* * * * *